United States Patent [19]

Houser

[11] Patent Number: 5,853,425
[45] Date of Patent: Dec. 29, 1998

[54] ELECTRODE CATHETER, IN PARTICULAR FOR TEMPORARY USE

[75] Inventor: Russ A. Houser, Livermore, Calif.

[73] Assignee: FIAB S.r.l., Florence, Italy

[21] Appl. No.: 833,656

[22] Filed: Apr. 8, 1997

[30] Foreign Application Priority Data

Apr. 10, 1996 [IT] Italy ............................ BO96A0197

[51] Int. Cl.$^6$ ........................................... A61N 1/05
[52] U.S. Cl. ........................................... 607/122
[58] Field of Search ................................. 607/122, 123, 607/124, 125, 126, 115, 116; 606/41

[56] References Cited

U.S. PATENT DOCUMENTS 4,639,252  1/1987  Kelly et al. .
5,363,861  11/1994  Edwards et al. .

FOREIGN PATENT DOCUMENTS 373953   6/1990   European Pat. Off. .
397173   11/1990  European Pat. Off. .
601806   6/1994   European Pat. Off. .
WO92/02272  2/1992   WIPO .
WO93/20878  10/1993  WIPO .

*Primary Examiner*—Scott M. Getzow
*Attorney, Agent, or Firm*—Fay, Sharpe, Beall, Fagan, Minnich & McKee

[57] ABSTRACT

An electrode catheter for temporary use comprises a biocompatible sheath with a distal end and a proximal end connected to means for commanding and controlling sent or recorded electrical signals; on the sheath is provided an ogive element, fitted to close the distal end, made of conductive material and connected with a first conducting wire so as to define a first electrical pole; a flexible reinforcing core integral with the ogive element to guarantee an ergonomic conformation of the sheath; a first metal ring fastened to the exterior of the sheath and connected to a second conducting wire extending inside the sheath so as to define a second pole, and lastly a spiral element, elastically yielding, set coaxially to the first wire and to the core and electrically isolated; this spiral element covers a length equal to the distance between the ogive element and the first ring allowing it to be deformed elastically with the related adaptation of the length both to the conformation, and to the variation in the conformation of a cardiac cavity, to provide a stable contact with a wall of the cardiac cavity itself.

10 Claims, 1 Drawing Sheet

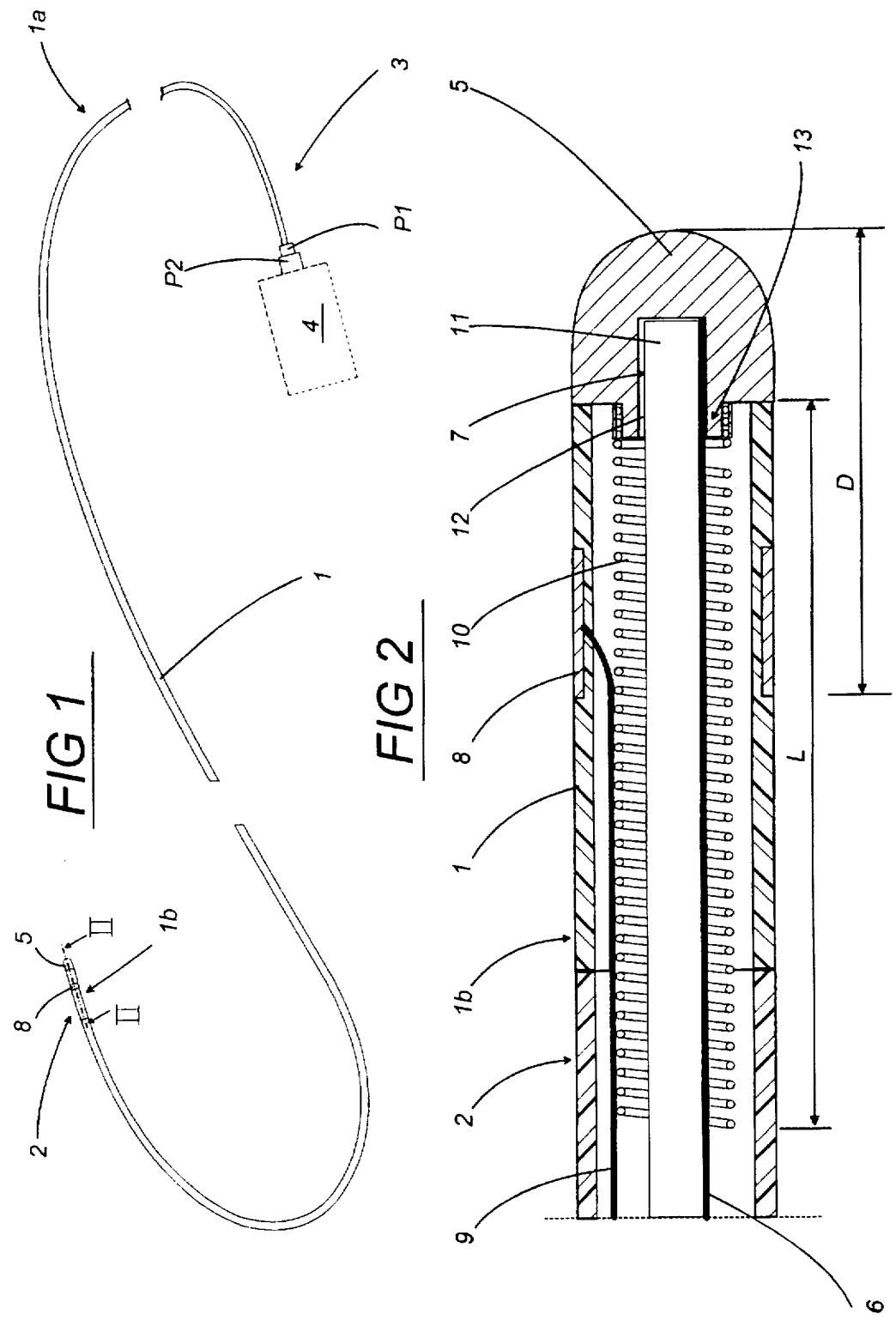

1

ELECTRODE CATHETER, IN PARTICULAR FOR TEMPORARY USE

BACKGROUND OF THE INVENTION

The present invention relates to an electrode catheter, in particular for temporary diagnostic and/or therapeutic use; essentially, it is an electro-medical apparatus which is used for cardiac diagnostic operations (verifying arrhythmias or other cardiac dysfunctions), or for temporary cardiac operations, such as the ablation of tissues and/or emergency cardiac stimulation.

Essentially two types of electrode catheters are currently in use: the definitive implant and the temporary implant, with temporary meaning an implant which is to remain in place, in the cardiac cavity, from a few hours to a few days (for a maximum duration of thirty days).

The subject of the present description is the second type of electrode catheters which are usually provided with an outer sheath made of biocompatible material at whose distal end is fitted a head electrode. This electrode is composed of an ogive element made of conducting metal which closes off the end of the sheath, whereas on the opposite side of the ogive (still inside the sheath) is connected a conducting wire which extends along the entire sheath to connect, in correspondence with the end of the sheath that is opposite to the ogive, to contacts present on command and control devices external to the sheath, so as to define a first electrical pole of the catheter.

Inside the sheath is usually fitted a core made up of a cylindrical conductor, isolated from said wire—first pole, whose function is to stiffen the catheter during the implantation phase (and whose secondary function is to protect the wire) and to define, where required, a conformation or shaping of the terminal portion of the catheter so that the latter, once the implantation has been completed, adapts inside the cardiac muscle in such a way as to copy the profile of the cardiac cavities: all for the purpose of obtaining a better contact with the walls of the cavities for the detection or generation of the desired signal.

In addition to what has just been described, additional electrical contacts are fitted in proximity to the distal end of the sheath and electrically isolated from the head ogive: each pole is obtained by means of a metal ring fastened to the outside of the sheath and connected to a related conducting wire extending inside the sheath until it connects with the related contacts.

An example of such solutions can be seen in the publication U.S. Pat. No. 5,363,861, which however is aimed at a technical solution which allows the physician to control the conformation of the distal part implanted, in order to adapt it in the best possible manner to the conformation of the cardiac muscle and to the specific requirements of the moment.

The problem stemming from known electrode catheters is directly linked to their design conformation and structure: as stated above, normally the distal part is pre-formed, with a series of curves with different radius (prepared directly by the producer), in order for the distal end to fit the cardiac cavity as well as possible, not taking into account, however, that inevitably the patient's heart will have non-standard dimensions or particular needs.

Pre-forming, moreover, requires the presence of a sufficiently rigid core, in order to maintain the desired conformation. These design peculiarities often fit poorly with the needs of a temporary implant, especially if the implant is aimed at checking cardiac functionality which requires, on one hand, an accurate and secure contact with the wall of the muscle and on the other hand, for the electrode catheter not to make its presence felt beyond the allowed limits, since cardiac physiology is often precarious.

If the electrode catheter is too soft, the diagnosing activity may be compromised; if, on the contrary, the electrode catheter is too stiff, precisely because it rests against the cardiac wall, it can compromise it or it may be pushed outside the heart as a consequence of its contractions which act on the electrode catheter with continuous peak loads.

SUMMARY OF THE INVENTION

The purpose of the present invention is therefore to construct a catheter whose distal portion, in proximity to the terminal end which is to be implanted inside the heart muscle, is easy to adapt, in the course of the operation, to the different conformations and sizes of the heart and is not affected by the heart's activity once it is implanted: in practice, the resulting catheter combines the characteristic of providing the secure detection-emission of the required electrical signal and the ease of adaptation to the continuous cardiac contractions, with minimized reaction forces.

This also in case of embodiments which entail the pre-forming of the distal portion of the electrode catheter.

BRIEF DESCRIPTION OF THE DRAWINGS

The technical characteristics of the invention, according to the purposes stated above, can be clearly noted from the content of the claims reported below and the advantages of the invention shall be made more evident in the detailed description which follows, made with reference to the enclosed drawings, which represent an embodiment provided purely by way of non limiting example, in which:

FIG. 1 depicts an electrode catheter for temporary use according to the present invention in a prospective view with some parts removed the better to show other parts;

FIG. 2 depicts a section II—II as per FIG. 1 in an enlarged scale.

DESCRIPTION OF THE PREFERRED EMBODIMENT

In accordance with the Figures of the accompanying drawings, the subject electrode catheter is used for temporary operations for diagnostic or operating purposes inside cardiac cavities: operations which can be the verification of arrhythmias or the ablation of cardiac tissues.

The electrode catheter comprises a tubular sheath 1 made of biocompatible material, which represents the outer body of the electrode catheter, and it has a distal end 2 and a proximal end 3; the distal end represents the operational part which is implanted into a cardiac cavity (not shown here), whereas the proximal end 3 is connected to means 4 for the command and control of electrical signals sent or recorded (such means are only rendered schematically in FIG. 1, since they are not strictly part of the present invention).

In FIG. 2, it is possible to observe the operational part of the electrode catheter, i.e. the distal end 2 of the sheath 1, where an ogive element 5, a flexible core 7, a first ring 8 and a spiral element 10 are present.

More in detail, the ogive element 5 is placed in correspondence with and as a closure to the distal end 2, and it is made of conductive material. To this ogive element 5 is connected a first conducting wire 6 which extends all the way to the proximal end 3 to define a first conducting pole P1 connected to said command and control means 4.

Said flexible core 7 is made of conductive material, it extends all the way to the proximal end 3 of the sheath 1, and is integral, with one of its ends, with the ogive element 5: the flexible core 7 in practice serves as an element reinforcing and shaping the sheath 1 to guarantee the definition of an ergonomic conformation of the sheath according to the development of said cardiac cavity.

This core 7 comprises a third metal wire 11 set inside a seat 12 obtained centrally on a cylinder 13 which is part of the ogive element 5.

Inside the seat 12 is inserted and fastened the end of the first wire 6, distanced radially from the third wire 11, but developing parallel to the third wire: in other words the first wire 6 is the pole P1 connecting the ogive 5 and the command and control means 4, while the third wire 11 acts as a safe conducting element and as an aid in forming the profiles which the electrode catheter needs to achieve inside the cardiac cavity.

Said first ring 8 is made of metallic material and it is fastened onto the exterior of the sheath 1 in the vicinity of the distal end 2 of the sheath.

The first ring 8 is connected to a second wire 9, conductive, which extends inside sheath 1 until it reaches the proximal end 3 to form a second electrical pole P2 to connect to said command and control means 4.

The spiral element 10 is made up of an elastically yielding spiral, which is inserted coaxially external to the first wire 6 and to the core 7. The spiral element 10 can simply be made to rest, with one of its ends, onto the head of the cylinder 13 of the ogive element 5, or alternatively it can be made integral with the ogive itself by means of crimping around said cylinder 13 to be securely fastened inside the distal end 2 (see continuous line in FIG. 2).

The spiral element 10, moreover, is electrically isolated in correspondence with its internal cylindrical surface set opposite to the core 7 and to the first wire 6 by means of covering the surface itself with an isolating material (such as Teflon): in this way, the signal which passes through the core 7 and the first wire 6 cannot be deteriorated or altered as a result of a contact with the spiral 10.

As can be clearly seen in FIG. 2, the spiral 10 develops preferably in correspondence with the distal end 2 for a length L which is longer than the distance, indicated as D, between the end of the ogive element 5 and the first ring 8: in this way the spiral 10 allows the distal tract 2 to be deformed elastically, with the subsequent adaptation of the length L encompassed by spiral 10, both to the conformation and to the variation of the conformation of the cardiac cavity which achieves a stable contact with a wall of the cardiac cavity itself.

In other words the spiral 10 allows a safe detection, or inputting, of the required electrical signal thanks to the elasticity of the spiral itself which adapts the distal end 2 to continuous cardiac contractions, by damping the reaction forces given by the cardiac contractions down to a minimal level.

To obtain a better adaptability of the electrode catheter to the different morphologies presented by cardiac cavities, the sheath 1 can be subdivided in two distinct parts, indicated as 1a and 1b: the larger portion 1a encompasses the proximal end 3 and a middle part of the sheath 1, while the smaller portion 1b defines the distal end 2 comprising the two poles P1 and P2 defined by the ogive element 5 and by the first ring 8.

The smaller portion 1b can be securely joined to the remainder of the sheath with no gaps through a gluing procedure or by fusing together the two portions.

The latter solution is preferable, since the spiral element 10 has an extension which is equal to or slightly larger than the smaller portion 1b, and it is therefore possible to assemble the smaller portion with diversified elements according to the various requirements which the manufacturer may face on a case by case basis.

In other words the electrode catheter can be manufactured according to specific requirements, changing, for instance, the type of core 7: for example, if a higher contact potential of the electrode catheter on the wall of the cardiac cavity is required, a third wire 11 will be inserted, with a larger diameter than a pre-set standard; another detail may be that of adding one or more conducting rings in correspondence with the distal portion to meet requirements for a larger signal strength of the catheter, or to be able to differentiate the electrical signals sent or received.

Additionally, the separate structure between the proximal portion and the distal portion allows to construct the electrode catheter with the specified materials and characteristics, and if need be to personalize it in the ergonomic configuration required by the physician.

The materials used, as mentioned previously, can differ in the various constructive elements present according to the particular requirements: the spiral element can be made of plastic material, or of stainless steel, or of nitinol (to obtain the utmost elasticity or for pre-forming with "thermal memory" effect); analogously, the third wire defining the core can be made of the same materials mentioned above for the spiral element.

The invention thus conceived can be subject to numerous modifications and variations without thereby departing from the scope of the inventive concept. Moreover, all components may be replaced with technically equivalent elements.

What is claimed:

1. An electrode catheter for temporary use which can be inserted in cardiac cavities, and which can be connected to means for commanding and controlling sent or recorded electrical signals, the electrode catheter comprising:

a biocompatible sheath having a distal end and a proximal end;

an ogive element placed in correspondence with and to close said distal end of said sheath, made of conductive material and to which is connected a first conducting wire which extends to said proximal end so as to define a first conducting pole adapted for connection to a command and control means, the ogive element having an end disposed internally to the sheath;

a reinforcing flexible core made of conductive material, placed internally to the sheath and extending to the proximal end of the sheath, and integral, with one of its ends, to said ogive elements;

the flexible core serving as a shaping element of the sheath, for guaranteeing the definition of an ergonomic conformation of said sheath according to the development of said cardiac cavity;

at least a first metal ring fastened to the exterior of said sheath in proximity with said distal end of the sheath itself, and connected to a second conducting wire extending inside said sheath to said proximal end so as to define a second pole; and a spiral element, electrically isolated, elastically yielding and shapable, inserted coaxially to said first wire and to said core, wherein the spiral element is removable and exchangeable, said spiral element extending at least in correspondence with said distal end for a length equal at least to a distance between said ogive element and said first ring to allow said distal end to be pre-shaped and elastically deformed, with subsequent adaptation of said length to a conformation and to a variation in the conformation of said cardiac cavity in order to provide a stable contact with a wall of the cardiac cavity.

2. The electrode catheter as defined by claim 1, wherein the spiral element rests securely on said internal end of said ogive element.

3. The electrode catheter as defined by claim 1, wherein said spiral element has two ends and is integral with one of its ends to said ogive element.

4. The electrode catheter as defined by claim 1, wherein said sheath is subdivided in two distinct portions including a larger portion which represents said proximal end and a middle part, and a smaller portion which defines said distal end which comprises said two poles, and which can be securely joined to the remainder of the sheath with no gaps.

5. The electrode catheter as defined by claim 1, wherein said sheath is subdivided in two distinct portions including a larger portion which represents said proximal end and a middle portion, and a smaller portion which defines said distal end which comprises said two poles, and which can be securely joined to the remainder of the sheath with no gaps said spiral element having an extension at least equal to said smaller portion.

6. The electrode catheter as defined by claim 1, wherein said core comprises a third metal wire set in a seat obtained centrally on a cylinder which is part of said ogive element within said seat being set the end of said first wire slightly removed from and parallel to said third wire.

7. The electrode catheter as defined by claim 1, wherein said spiral element is electrically isolated at least in correspondence with the internal cylindrical surface opposite to said core and said first wire by means of covering the surface itself with an isolating material.

8. The electrode catheter as defined by claim 1, wherein said core is made of plastically yielding and shapable material, whereby it can be shaped and developed in a manner that is ergonomically suited to the cardiac cavity.

9. The electrode catheter as defined by claim 1, wherein the spiral element is integral with and wound around said internal end of the ogive element.

10. An electrode catheter for temporary use which can be inserted in cardiac cavities and which can be connected to means for commanding and controlling sent or recorded electrical signals, the electrode catheter comprising:

a biocompatible sheath subdivided in two portions, a first portion represents a proximal end and a middle part, and a second portion defines a distal end which includes two poles, and which can be securely joined to the remainder of the sheath with no gaps;

an ogive element placed in correspondence with and close to said distal end of said sheath, made of conductive material and to which is connected a first conducting wire extending all the way to said proximal end so as to define a first conducting pole connected to said command and control means, the ogive element having a protuberance disposed internally to the sheath;

a reinforcing flexible core made of conductive and plastically yielding material, placed internally to the sheath and extending all the way to the proximal end of the sheath, and integral, with one of its ends, to said ogive element, the flexible core serving as shaping element of the sheath, wherein it is guaranteed a definition of an ergonomic conformation of said sheath according to the development of the cardiac cavity;

at least a first metal ring fastened to the exterior of said sheath in proximity to said distal end of the sheath itself, and connected to a second conducting wire extending inside said sheath all the way to said proximal end so as to define a second pole; and, a spiral element being electrically isolated and elastically yielding, inserted coaxially to said first wire and to said core, resting on the protuberance of the ogive element, wherein the spiral element is removable and exchangeable, said spiral element extending at least in correspondence with said distal end for a length equal at least to a distance between said ogive element and said first ring to allow said distal end to be elastically deformed, with subsequent adaption of said length to the conformation and to the variation in the conformation of said cardiac cavity in order to provide a stable contact with a wall of the cardiac cavity.

* * * * *